US010234400B2

(12) United States Patent
Ahner et al.

(10) Patent No.: US 10,234,400 B2
(45) Date of Patent: Mar. 19, 2019

(54) FEATURE DETECTION WITH LIGHT TRANSMITTING MEDIUM

(71) Applicant: Seagate Technology LLC, Cupertino, CA (US)

(72) Inventors: Joachim Walter Ahner, Livermore, CA (US); Florin Zavaliche, San Ramon, CA (US); David M. Tung, Livermore, CA (US); Samuel Kah Hean Wong, Johor (MY); Maissarath Nassirou, Fremont, CA (US); Henry Luis Lott, Fremont, CA (US); Stephen Keith McLaurin, Sunnyvale, CA (US)

(73) Assignee: Seagate Technology LLC, Cupertino, CA (US)

( * ) Notice: Subject to any disclaimer, the term of this patent is extended or adjusted under 35 U.S.C. 154(b) by 332 days.

(21) Appl. No.: 14/053,493

(22) Filed: Oct. 14, 2013

(65) Prior Publication Data

US 2014/0104603 A1   Apr. 17, 2014

Related U.S. Application Data

(60) Provisional application No. 61/714,170, filed on Oct. 15, 2012.

(51) Int. Cl.
*G01N 21/95* (2006.01)
*G01B 11/24* (2006.01)
*G01N 21/47* (2006.01)

(52) U.S. Cl.
CPC ............. *G01N 21/95* (2013.01); *G01B 11/24* (2013.01); *G01N 21/47* (2013.01)

(58) Field of Classification Search
CPC .... G01N 21/88–21/8851; G01N 21/93; G01N 21/94; G01N 21/95–21/951
See application file for complete search history.

(56) References Cited

U.S. PATENT DOCUMENTS

| 3,623,809 A | * | 11/1971 | Diprose | ................. | G02B 27/28 355/38 |
| 3,729,636 A | * | 4/1973 | Merker | ................. | A24C 5/3412 131/283 |
| 4,087,685 A | * | 5/1978 | Froot | ................. | G01N 21/64 250/302 |
| 4,543,574 A | * | 9/1985 | Takagi | ................. | G02B 6/2804 370/462 |
| 4,737,004 A | | 4/1988 | Amitay et al. | | |
| 5,329,351 A | * | 7/1994 | Clementi | ................. | G01N 21/88 250/208.2 |

(Continued)

FOREIGN PATENT DOCUMENTS

| CN | 2238435 Y | 10/1996 |
| CN | 2433619 Y | 6/2001 |

(Continued)

*Primary Examiner* — Tri Ton
*Assistant Examiner* — Rufus Phillips

(57) ABSTRACT

An apparatus for detecting surface features is disclosed. The apparatus may include a plurality of strands configured to contain light and further configured to transmit light from a light source to a surface of an article. The apparatus may also include a detector configured to receive light reflected from the surface of the article via the plurality of strands, wherein the detector is further configured to detect features associated with the article.

8 Claims, 14 Drawing Sheets

(56) References Cited

U.S. PATENT DOCUMENTS

| | | | | |
|---|---|---|---|---|
| 5,506,676 | A * | 4/1996 | Hendler | G01R 31/308 |
| | | | | 250/559.09 |
| 5,519,526 | A * | 5/1996 | Chua | H04J 14/005 |
| | | | | 398/139 |
| 5,534,997 | A * | 7/1996 | Schrader | G01N 21/65 |
| | | | | 356/301 |
| 5,661,559 | A | 8/1997 | Brezoczky et al. | |
| 5,875,029 | A * | 2/1999 | Jann | G01N 21/94 |
| | | | | 356/237.2 |
| 6,128,078 | A * | 10/2000 | Fateley | G01J 3/02 |
| | | | | 356/328 |
| 6,370,406 | B1 * | 4/2002 | Wach | G01N 21/474 |
| | | | | 356/301 |
| 6,781,699 | B2 | 8/2004 | Dunn et al. | |
| 6,975,388 | B2 * | 12/2005 | Frot | G01N 21/431 |
| | | | | 356/128 |
| 7,292,330 | B2 * | 11/2007 | Saunders | G01N 21/956 |
| | | | | 250/216 |
| 7,405,825 | B2 * | 7/2008 | Schuurmans | G01J 3/02 |
| | | | | 356/326 |
| 7,864,316 | B2 * | 1/2011 | Lewis | B01F 9/04 |
| | | | | 356/300 |
| 8,115,932 | B2 * | 2/2012 | Moll | G01N 21/55 |
| | | | | 356/320 |
| 9,068,917 | B1 * | 6/2015 | Vaez-Iravani | G01N 21/00 |
| 2004/0208458 | A1 * | 10/2004 | Uno | G02B 6/4214 |
| | | | | 385/89 |
| 2007/0052955 | A1 | 3/2007 | Shishido et al. | |

FOREIGN PATENT DOCUMENTS

| | | |
|---|---|---|
| CN | 101762566 A | 6/2010 |
| CN | 202442950 U | 9/2012 |
| CN | 202794062 U | 3/2013 |
| JP | H03-96903 A | 4/1991 |
| JP | H08-334648 A | 12/1996 |
| JP | 63-256723 A | 10/1998 |
| JP | H10-332348 A | 12/1998 |
| JP | 2002-350283 A | 12/2002 |
| JP | 2003-255195 A | 9/2003 |
| JP | 2010-256148 A | 11/2010 |
| JP | 2012-063209 A | 3/2012 |
| WO | 9852025 A1 | 11/1998 |

\* cited by examiner

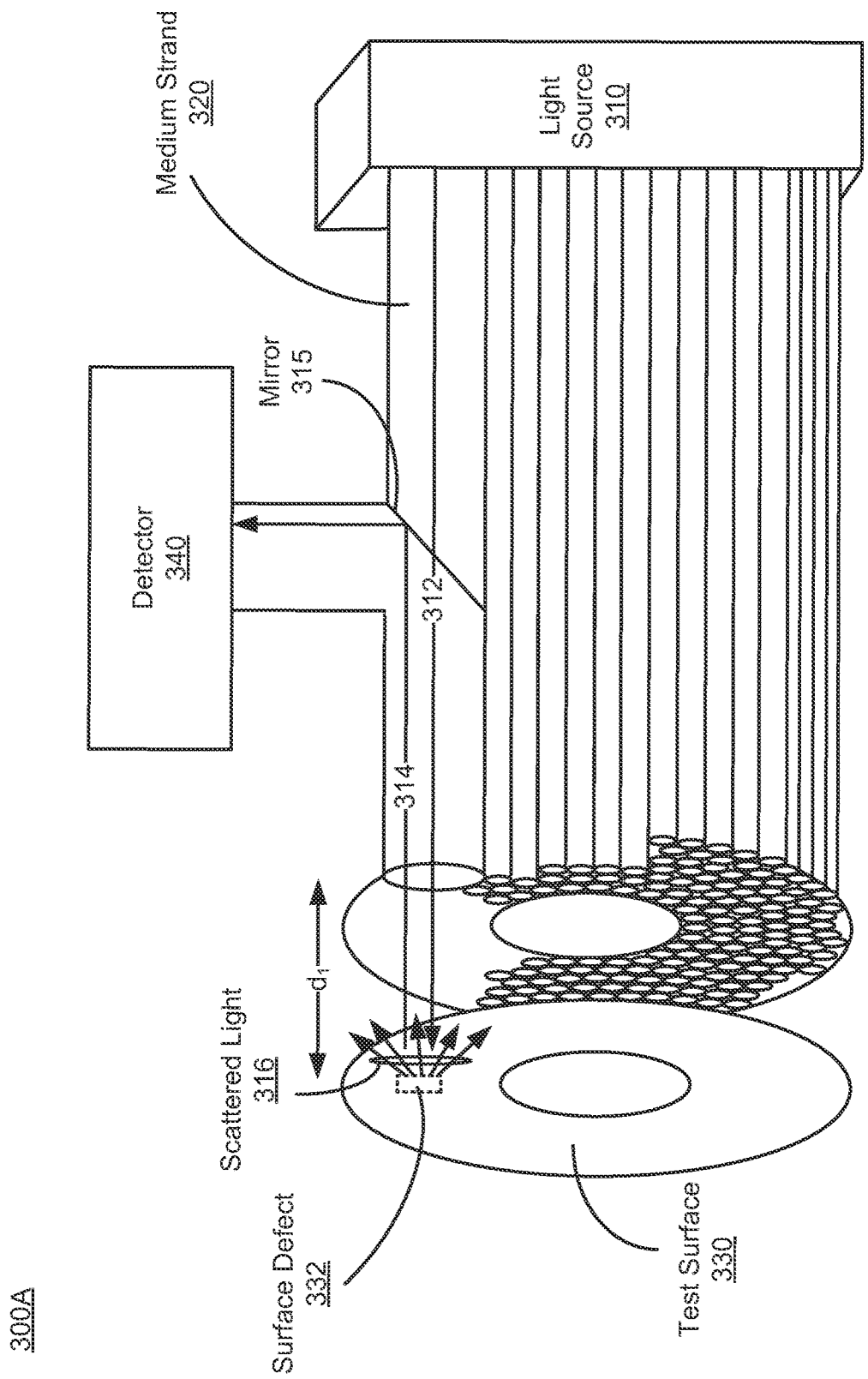

FEATURE DETECTION WITH LIGHT TRANSMITTING MEDIUM

RELATED APPLICATIONS

This application claims the benefit of and priority to U.S. Provisional Patent Application filed on Oct. 15, 2012 with the application No. 61/714,170, which is incorporated by reference in its entirety.

BACKGROUND

In general, during quality assurance, a product is inspected to detect defects. The product, for example, a disk, wafer, or media, may be one of many products that are inspected. Over the years, products have become smaller and continue to get smaller. Accordingly, their defects are also becoming smaller and more difficult to detect.

Defects may result from particle contaminants that are trapped on the surface of the product, e.g., a disk, wafer, media, etc. The trapped particle may damage the sputtered film of the product. Furthermore, particles may contaminate the finished surface and lead to scratch formation and debris generation. In a disk drive technology, defects such as particle contaminants may adversely impact the media head spacing.

SUMMARY

According to one embodiment, an apparatus for detecting features of a product is disclosed. In one embodiment, the apparatus may include a plurality of strands configured to contain light and further configured to transmit light from a light source to a surface of an article. The apparatus may also include a detector configured to receive light reflected from the surface of the article via the plurality of strands, wherein the detector is further configured to detect features associated with the article.

These and various other features and advantages will be apparent from a reading of the following detailed description.

BRIEF DESCRIPTION OF DRAWINGS

FIGS. 3A and 3B show an apparatus for detecting a height associated with a feature on a surface of an article according to one embodiment.

DETAILED DESCRIPTION

Before some particular embodiments are described in greater detail, it should be understood by persons having ordinary skill in the art that the particular embodiments do not limit the concepts described and/or illustrated herein, as elements in such embodiments may vary. It should likewise be understood that a particular embodiment described and/or illustrated herein has elements which may be readily separated from the particular embodiment and optionally combined with any of several other embodiments or substituted for elements in any of several other embodiments described herein.

It should also be understood by persons having ordinary skill in the art that the terminology used herein is for the purpose of describing the particular embodiments, and that the terminology is not intended to be limiting. Unless indicated otherwise, ordinal numbers (e.g., first, second, third, etc.) are used to distinguish or identify different elements or steps in a group of elements or steps, and do not supply a serial or numerical limitation on the elements or steps. For example, "first," "second," and "third" elements or steps need not necessarily appear in that order, and embodiments need not necessarily be limited to three elements or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

Unless defined otherwise, all technical and scientific terms used herein have the same meaning as commonly understood by persons of ordinary skill in the art.

According to some embodiments, a light source emits optical signals, e.g., light, onto the surface of the article, e.g., a semiconductor wafer, a disk, a media, etc. Light is transmitted from the light source to the article via medium strands, e.g., fiber optics, glass optics, etc. Light reflected from the surface of the article is captured and subsequently transmitted to the detector via the medium strands. The detector may analyze the reflected light in order to identify features of the article, e.g. defects, height of a defect, etc. Accordingly, the article of interest may be tested and certain features of the article may be identified.

Figure 1A:
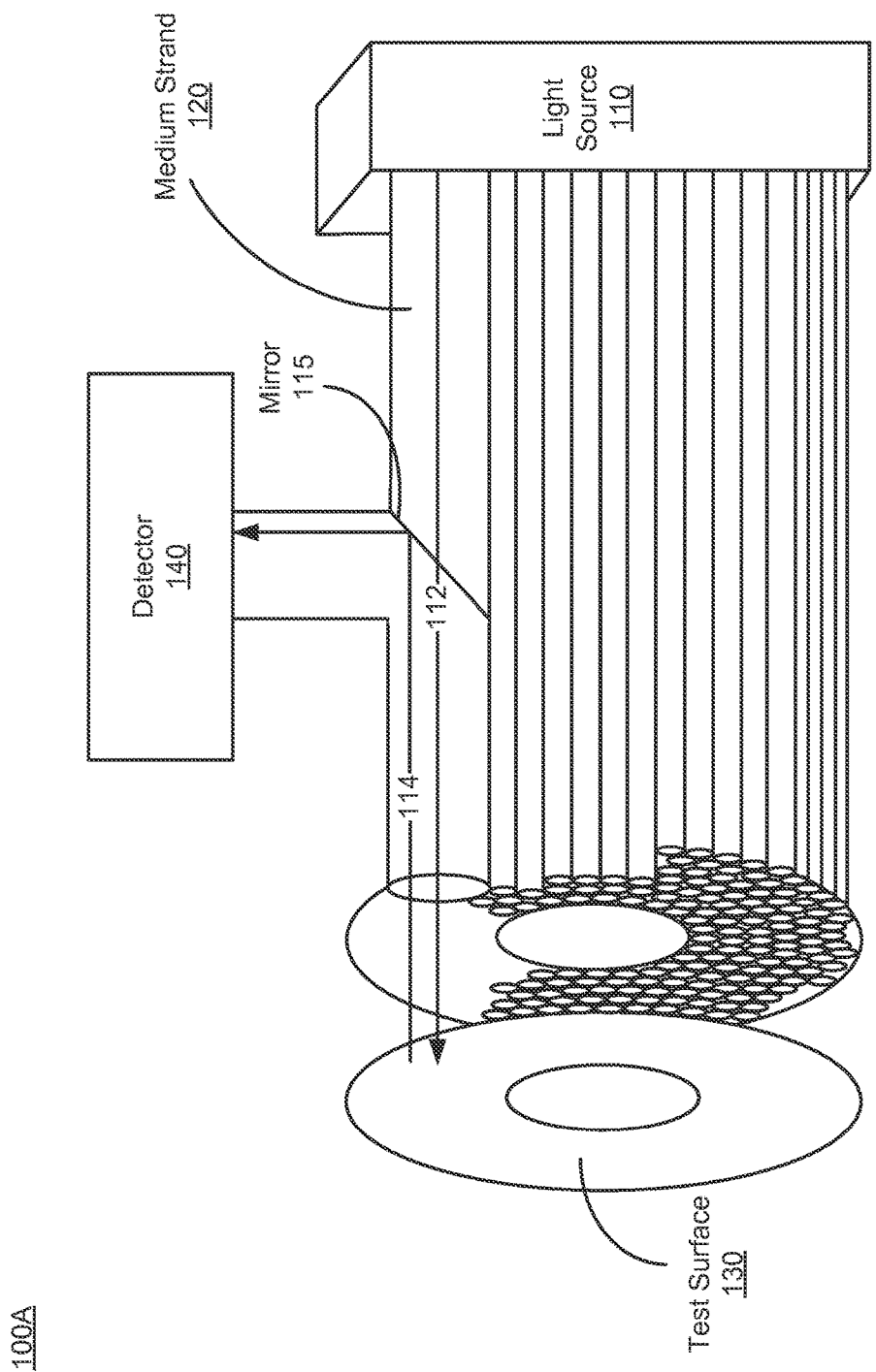
FIG. 1A shows an apparatus for detecting a defect on an article according to one embodiment.

Referring now to FIG. 1A, an apparatus for detecting a defect on an article according to one embodiment 100A is shown. The apparatus may include a light source 110, a detector 140, and one or more medium strands 120 coupling the light source 110 and the detector 140 to the article for testing, generally referred to as the test surface 130. It is appreciated that the article for testing may be a semiconductor wafer, a disk, media, etc.

According to some embodiments, the light source 110 shines light onto the surface of the article (also referred to as test surface 130). Light is transmitted from the light source 110 to the test surface 130 via medium strands 120. Light reflected from the surface of the test surface 130 is captured by the medium strands 120 and subsequently transmitted to the detector 140 via the medium strands 120. The detector 140 may analyze the reflected light in order to identify features of the test surface 130. The features may include but are not limited to surface and/or subsurface defects that might degrade the performance of the article. According to one embodiment, surface and/or subsurface defects include particle and stain contamination, as well as defects including scratches and voids. It is appreciated that defect detection used throughout the application is an example of identifying features of the article and is not intended to limit the scope of the embodiments described herein.

In one embodiment, the light source 110 is configured to emit light. It is appreciated that the light source 110 may be a wide light source. In various embodiments, the light source 110 may be configured to have certain characteristics, e.g., coherent light, incoherent light, polarized light, non-polarized light, different wavelengths, etc. It is appreciated that the light source 110 may provide light with a combination of different characteristics, e.g., coherent light at different wavelengths, coherent and incoherent light simultaneously with a user selectable polarization, etc. According to some embodiments light characteristic features may be user selectable.

Various light characteristics may be used to identify different defects in the article. In one example, incoherent light may be suitable for providing parallel illumination of the article under examination for detecting defects of a first type while coherent light at a particular wavelength may be suitable for providing parallel illumination of the article under examination for detecting defects of a second type.

According to some embodiments, the medium strands 120 may be a medium that can contain and transmit light from one location to another. For example, the medium strands 120 may include fiber optic cables, glass fibers, etc. It is appreciated that the diameter of the medium strands 120 may vary depending on test application. It is also appreciated that medium strands 120 with different diameters may be used for the same test. In some embodiments, the medium strands 120 may include a mirror 115, e.g., a half mirror. The mirror 115 may be coated with an optical coating and oriented such that it is transmissive with respect to the light 112 from the light source 110 while it is reflective with respect to the light 114 being reflected from the test surface 130. The mirror 115 may be oriented in such a way that the reflected light is directed toward the detector 140 for analysis. It is appreciated that while only one medium strand 120 is shown with the mirror 115 other medium strands 120 may similarly include the mirror 115.

According to some embodiments, the optical coating may include a metallic coating, a dielectric optical coating, or a combination thereof. In some embodiments, for example, the metallic coating includes an aluminum coating. In some embodiments, for example, the dielectric optical coating includes magnesium fluoride, calcium fluoride, various metal oxides, and any combination thereof.

According to some embodiments, combinations of metallic and dielectric optical coatings may also be used. For example, a metallic coating, e.g., aluminum coating, may be used as a base coating and a dielectrical optical coating may be used as one or more additional coatings. In another embodiment, for example, the optical coating may include a dielectrical optical coating as a base coating and one or more additional dielectric coatings thereon.

The number of optical coatings (e.g., one, two, three, four, five, etc.), the composition (e.g., aluminum, magnesium fluoride, calcium fluoride, various metal oxides, etc.) of each optical coating, and the thickness of each optical coating may be tailored to provide a desired reflectivity and/or transmitivity. For example, the half mirror 115 may be configured to reflect at least 40%, 45%, 50%, 55%, 60%, 65%, 70%, 75%, 80%, 85%, 90%, 95%, or 99% of the light reflected from the test surface 130 toward the detector 140. In some embodiments, the reflectivity of the optical coating on the half mirror 115 may be no more than 99.9%, 95%, 90%, 85%, 80%, 75%, 70%, 65%, 60%, 55%, 50%, or 45%. Combinations of the foregoing may also be used to describe the reflectivity of the optical coating on the half mirror. In some embodiments, for example, the reflectivity of the optical coating on the half mirror may be at least 40% and no more than 99.9% (i.e., between 40% and 99.9%), such as at least 50% and no more than 99.9% (i.e., between 50% and 99.9%), at least 60% and no more than 99.9% (i.e., between 60% and 99.9%) or at least 75% and no more than 99.9% (i.e., between 75% and 99.9%). It is appreciated that the mirror 115 may similarly be configured with its coating to have a particular transmissive property, e.g., at least 60%, 70%, 80%, 90%, 95%, 99%, etc.

In various embodiments, the medium strands 120 may be a 'T'-shaped optic fiber having a first portion, terminating in a first terminus, a second portion, terminating in a second terminus, and a third portion, terminating in a third terminus. The first terminus of a 'T'-shaped optic fiber may be oriented toward the light source 110 such that it is able to transmit incident light 112 from the light source 110. The second terminus of a 'T'-shaped optic fiber may be oriented toward the test surface 130 under examination such that it is able to transmit light from the light source 110 to the test surface 130 and capture light reflected from the test surface 130 under examination. The third terminus of a 'T'-shaped optic fiber may be oriented toward the detector 140 to transmit light reflected from the test surface 130 under examination to the detector.

In one embodiment, the third portion of a 'T'-shaped optic fiber includes a half-mirror 115 in the end opposite to the third terminus, the end opposite the third terminus being the half-mirror 115 end. The half-mirror 115 end of the third portion may be spliced into the optic fiber including the first and second portions such that the resulting 'T'-shaped optic fiber is configured to transmit light and reflected light as described herein. A multitude of optic fibers may be spliced in accordance with the foregoing and aggregated to provide an array of 'T'-shaped optic fibers in accordance with embodiments described herein. Such an array of 'T'-shaped optic fibers may be suitable for providing parallel illumination of the article under examination.

According to some embodiments, the detector 140 may receive the optical signals, e.g., reflected light from the test surface 130, that are reflected from the mirror 115. The detector 140 may analyze the received light or optical signals in order to determine whether the test surface 130 contains any defects. The detector 140 may include a computer or equivalent device and/or a photon-sensing array operable to detect parallel reflection of light from the test surface 130. Such a photon-sensing array may include a multitude of channels, wherein each channel of the photon-sensing array (e.g., multichannel detector) may correspond to a single optic fiber of the array of optic fibers, and wherein each optic fiber of the array of optic fibers may correspond to a particular location on the test surface 130. In some embodiments, one or more charge-coupled devices ("CCD"), complementary metal oxide-semiconductors ("CMOS"), or scientific complementary metal-oxide-semiconductors ("sCMOS") of sufficient sensitivity may be used in order to enable the detector to determine the location of defects. In some embodiments, a photomultiplier may be used to amplify the detected signal. A photomultiplier channel may be used for each optical fiber and, as such, for each channel of the photon-sensing array (e.g., multichannel detector). For example, in some embodiments, the multichannel detector comprises a high-resolution CMOS or an electron-multiplying charge-coupled device ("EMCCD") or a camera.

Figure 1B:
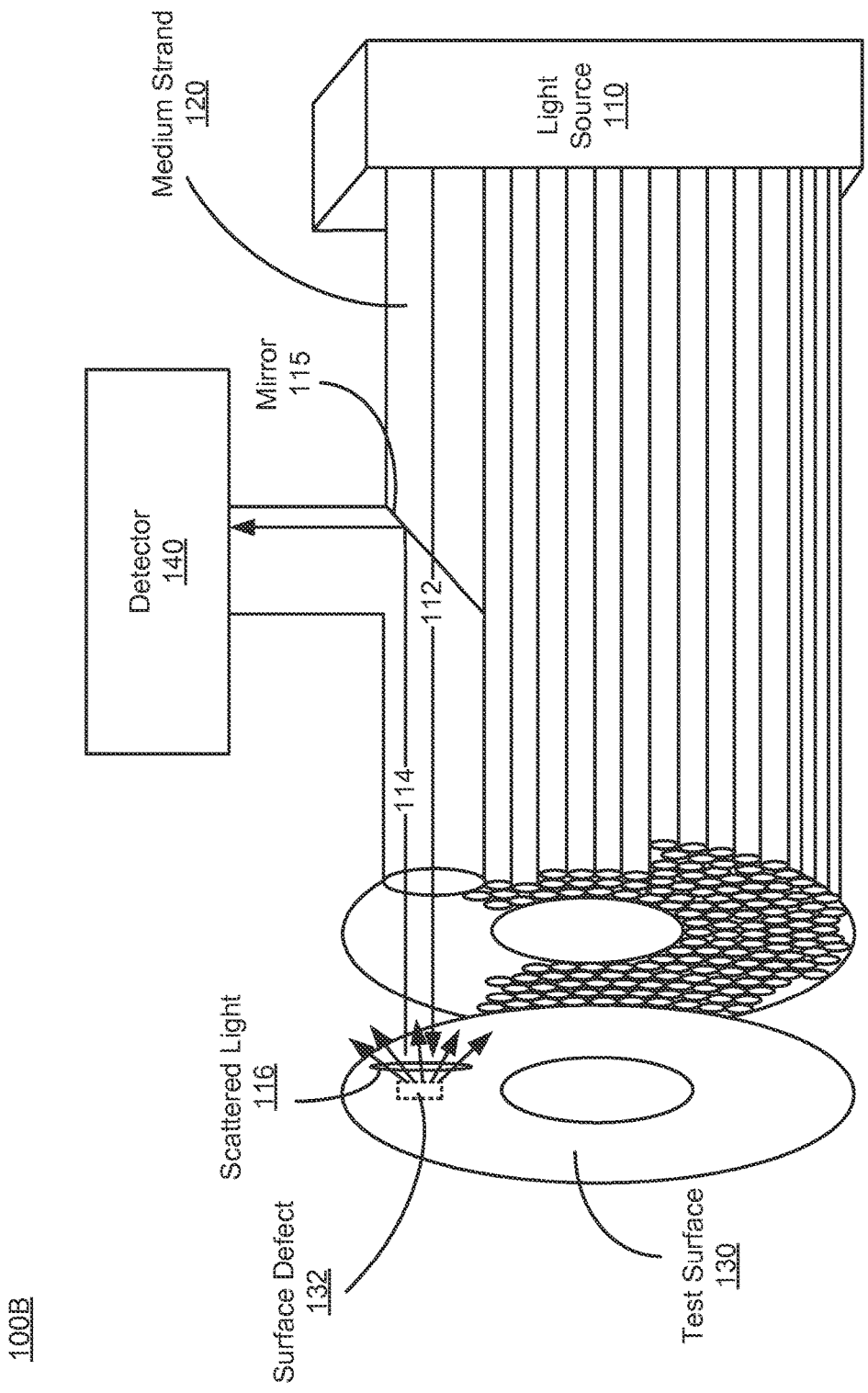
FIG. 1B shows an apparatus for detecting a feature on an article where the defect is present according to one embodiment.

According to some embodiments, light intensity may be used in order to determine whether a defect is present. For example, it may be deduced that very little of the incident light 112 has been scattered, as shown in embodiment 100A, and that the test surface 130 is therefore defect free because the light intensity of the light received by the detector 140 is within an acceptable threshold of the light intensity of the incident light 112. However, it may be deduced that the test surface 130 contains a surface defect 132 if the light intensity detected by the detector 140 is not within the acceptable threshold, e.g., lower light intensity, of the light intensity of the incident light 112 because of light scattering 116 resulting from the defect 132, as shown in FIG. 1B and embodiment 100B. It is appreciated that in other embodiments, higher light intensity may indicate presence of a defect depending on the light characteristics, e.g., coherent light, incoherent light, polarized light, non-polarized light, different wavelengths, etc.

While not shown in the schematic, the embodiments describe herein utilize a means for mounting and unmounting articles, e.g., disk, media, semiconductor wafer, etc. Moreover, the embodiments describe herein utilize means for moving or adjusting the articles, moving or adjusting the light sources, moving or adjusting the detector, detecting article defects, determining whether article defects are organic or inorganic based upon whether reflected light is elastic or inelastic, light intensity of reflected light, capturing data regarding article defects, cataloging data regarding article defects, analyzing data regarding defects, and/or the like.

It is appreciated that a computer or an equivalent device (i.e., a device including a processing element and memory operable to carry out arithmetic and logical operations) may be used in different aspects of the embodiments described herein. For example, in some embodiments, a computer may be used to operate the apparatus, including, but not limited to, mounting and unmounting articles for examination, rotating articles (if needed or desired), moving the light source, moving or adjusting the photon-sensing array, detecting article defects, determining whether article defects are organic or inorganic based upon whether reflected light is elastic or inelastic, light intensity of reflected light, capturing data regarding defects in articles, cataloging data regarding defects in articles, analyzing data in regarding defects in articles, and/or the like.

Figure 1C:
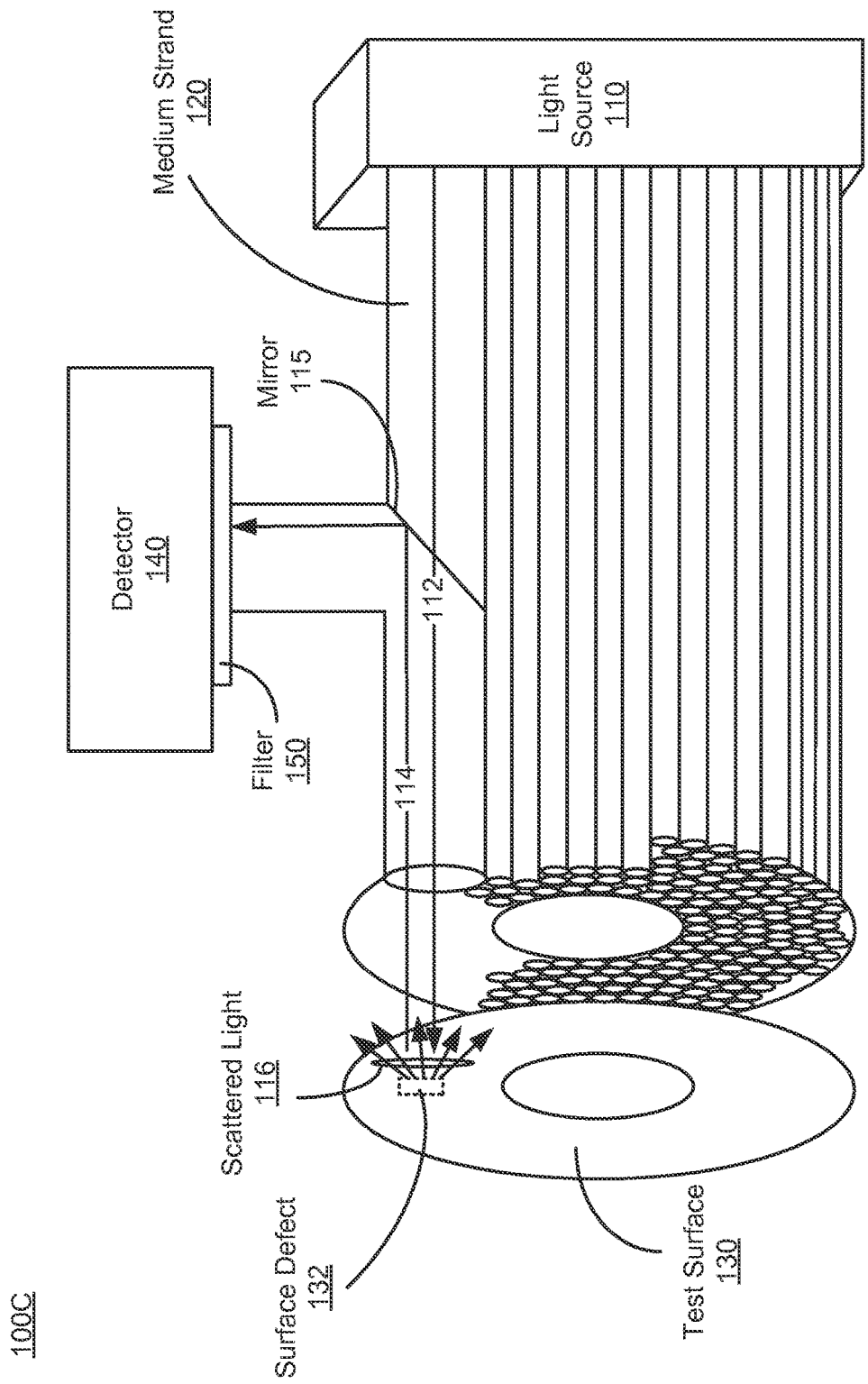
FIG. 1C shows an apparatus with a filter for detecting a feature on an article according to one embodiment.

Referring now to FIG. 1C, an apparatus with a filter for detecting a feature on an article according to one embodiment is shown. Embodiment 100C is substantially similar to that of 100B. In this embodiment, a filter 150 may be used to separate and filter out light with predetermined wavelengths. For example, blue light with a predetermined wavelength may be separated from red light with a predetermined wavelength. It is appreciated that the filter type may be user selectable. The filter type, e.g., band pass filter, wavelength filter, piezoelectric-tunable wavelength filter, coherence filter, phase filter, wave plate, polarization filter, piezoelectric-tunable polarization filter, etc., may be selected based on the type of defect one is searching for and it may further be based on the light source 110 type. According to one embodiment, filter 150 may be placed between the third terminus of the 'T'-shaped array of optic fibers and the photon-sensing array to discriminate wavelength and/or coherence of the light reflected from the article under examination. However, it is appreciated that other embodiments may include a filter 150 positioned elsewhere, e.g., positioned between the first terminus of the 'T'-shaped array of optic fibers from the light source 110 to the mirror 115.

According to one embodiment, a filter type e.g., band pass filter, wavelength filter, piezoelectric-tunable wavelength filter, coherence filter, phase filter, wave plate, polarization filter, piezoelectric-tunable polarization filter, etc., may be used to determine whether the light reflected from the article under examination, e.g., test surface 130, is elastic or inelastic. Determining whether the reflected light is elastic or inelastic may be used to determine whether the detected defect is inorganic or organic, respectively. For example, the wavelength of light scattered from the presence of an organic defect may not be preserved. As such, detection of inelastic light reflected from the test surface 130 may lead one to identify the presence of organic defects. Alternatively, the wavelength of light scattered by the presence of inorganic defect may be preserved. As such, detection of elastic light reflected from the test surface 130 may lead one to identify the presence of inorganic defects.

Figure 1D:
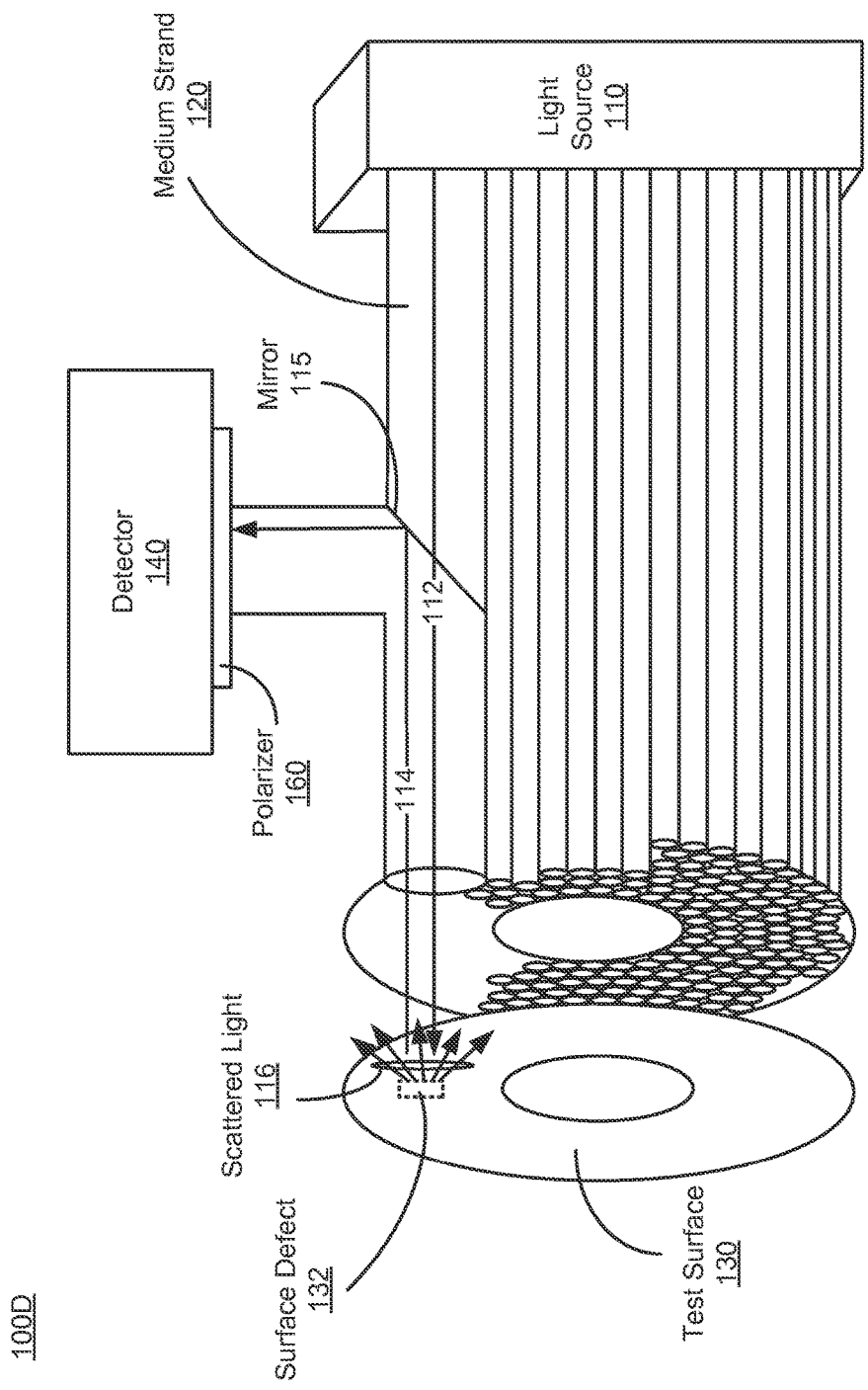
FIG. 1D shows an apparatus with a polarizer for detecting a feature on an article according to one embodiment.

Referring now to FIG. 1D, an apparatus with a polarizer for detecting a feature of an article according to one embodiment is shown. Embodiment 100D is substantially similar to that of 100B. In this embodiment, a polarizer 160, e.g., linear polarizer, circular polarizer, polarization filter, piezoelectric-tunable polarization filter, etc., may be used to pass light with a predetermined polarization while it blocks light with other polarization. It is appreciated that the polarizer type may be user selectable. The polarizer type may be selected based on the type of defect one is searching for and it may further be based on the light source 110 type. According to one embodiment, the polarizer 160 may be placed between the third terminus of the 'T'-shaped array of optic fibers and the photon-sensing array to discriminate polarization and/or coherence of the light reflected from the article under examination. However, it is appreciated that other embodiments may include a polarizer 160 positioned elsewhere, e.g., positioned between the first terminus of the 'T'-shaped array of optic fibers from the light source 110 to the mirror 115.

Figure 1E:
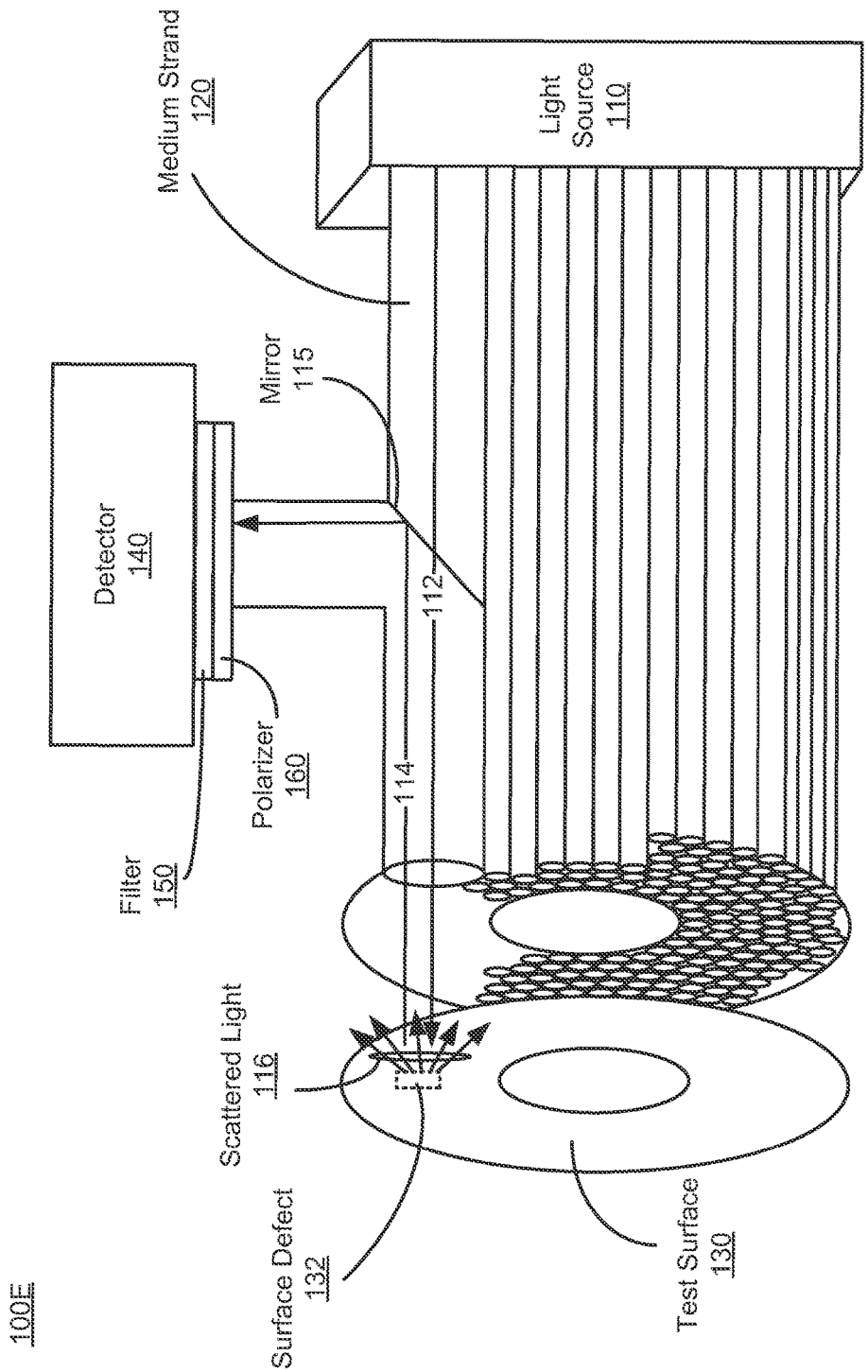
FIG. 1E shows an apparatus with a filter and a polarizer for feature a defect on an article according to one embodiment.

Referring now to FIG. 1E, an apparatus with a filter and a polarizer for detecting a feature of an article according to one embodiment is shown. Embodiment 100E is substantially similar to that of 100B, however, it includes both the filter 150 and the polarizer 160. It is appreciated the polarizer 160 and the filter 150 operate substantially similar to the embodiments 100C and 100D described above. It is appreciated that the order of the filter 150 and the polarizer 160 may vary depending on their application. Furthermore, it is appreciated that the filter 150 and the polarizer 160 may be positioned elsewhere, e.g., positioned between the first terminus of the 'T'-shaped array of optic fibers from the light source 110 to the mirror 115.

Figure 1F:
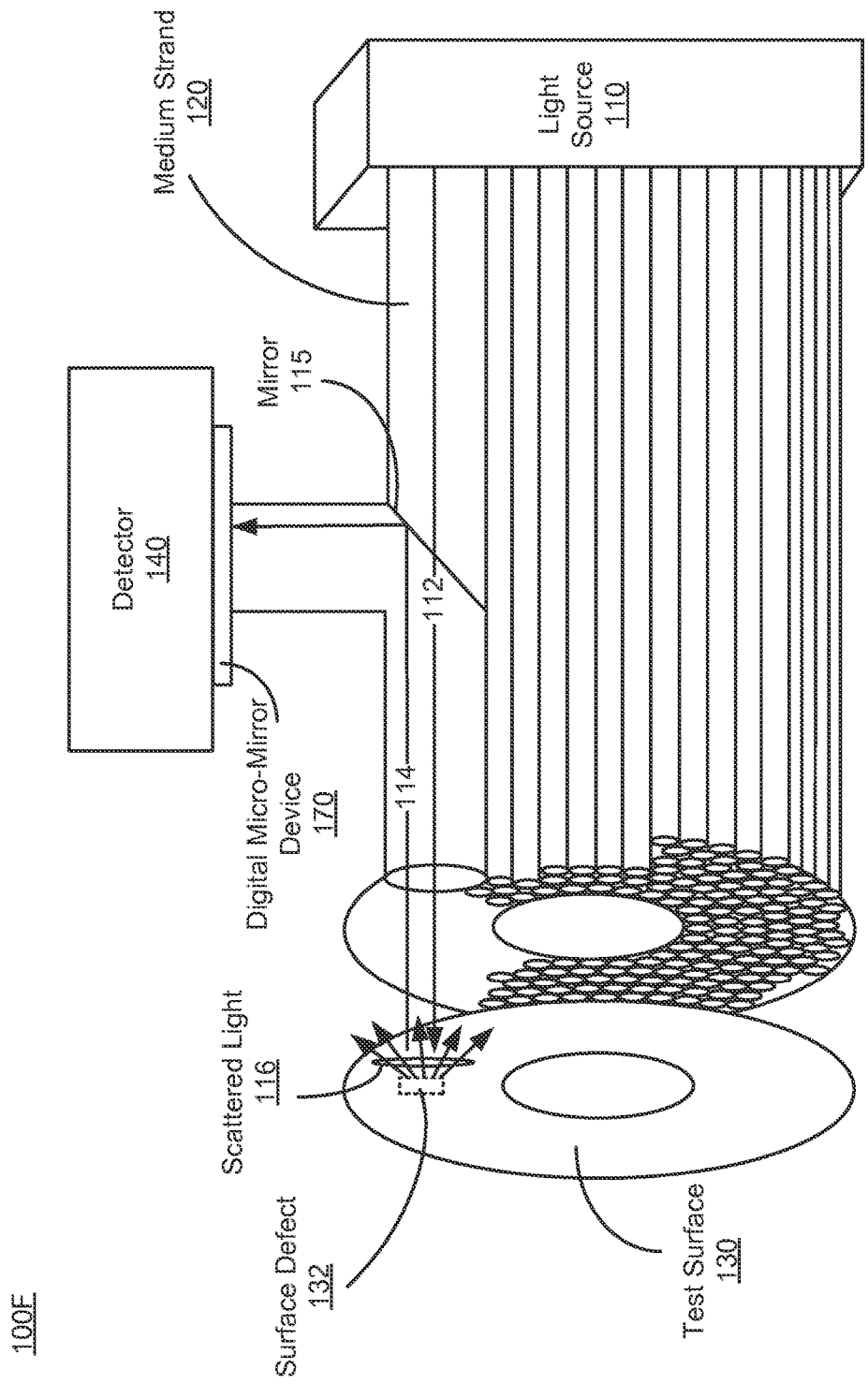
FIG. 1F shows an apparatus with a digital micro-mirror device for detecting a feature on an article according to one embodiment.

Referring now to FIG. 1F, an apparatus with a digital micro-mirror device for detecting a feature of an article according to one embodiment is shown. Embodiment 100F is substantially similar to that of 100B. However, in this embodiment, a digital micro-mirror device 170 may be coupled to the detector 140. The digital micro-mirror device 170 may be used to modulate the reflected light from the test surface 130. Signal modulation may be used to improve signal to noise ratio of the light reflected from the test surface 130. It is further appreciated that the digital micro-mirror device 170 may be used to steer the optical signals in different directions, e.g., the blue light may be steered in one direction while the red light is steered in a different direction. It is appreciated that the digital micro-mirror device 170 may be positioned elsewhere, e.g., positioned between the first terminus of the 'T'-shaped array of optic fibers from the light source 110 to the mirror 115.

Figure 1G:
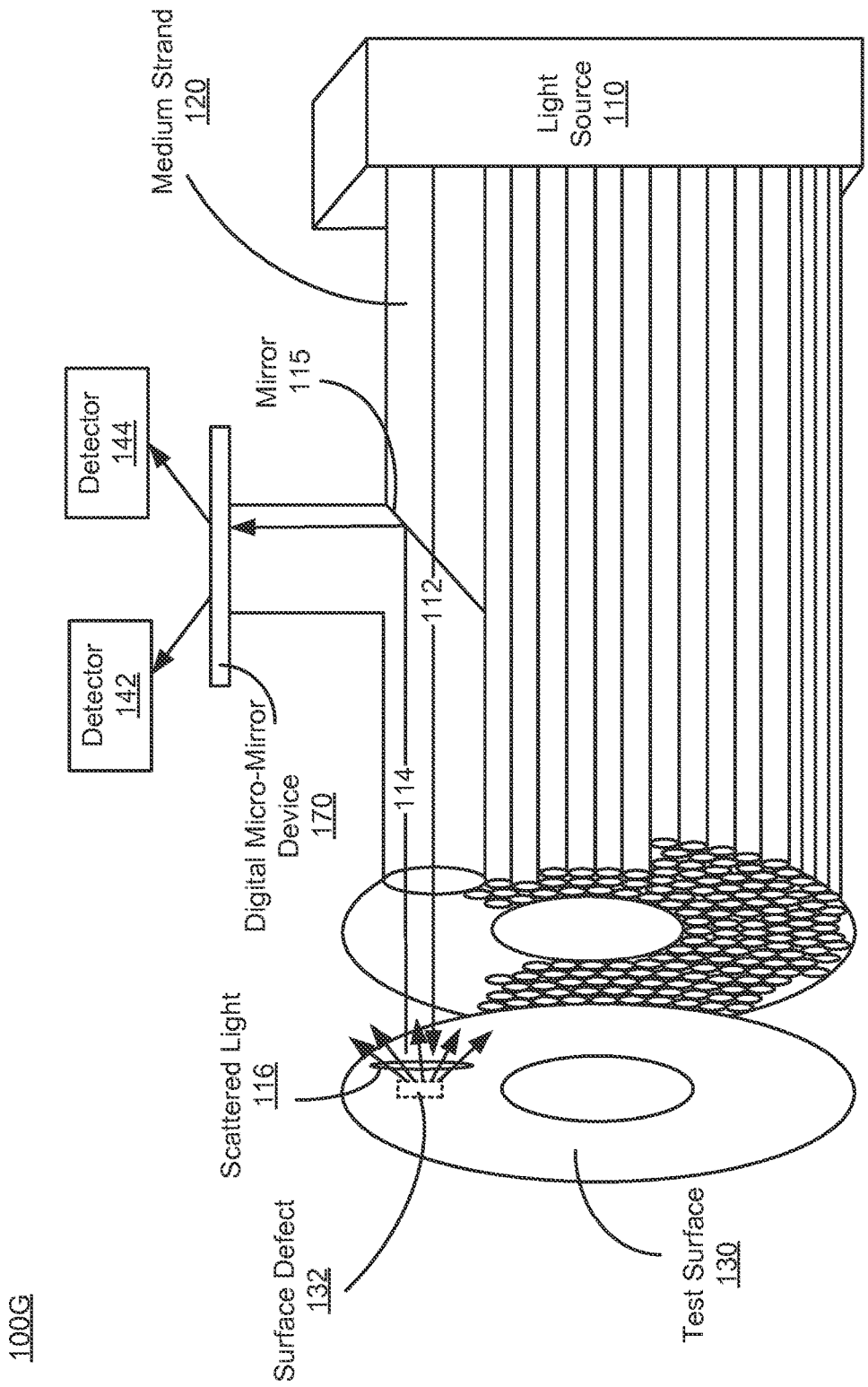
FIG. 1G shows an apparatus with a digital micro-mirror device and multiple detectors for detecting a feature on an article according to one embodiment.

Referring now to FIG. 1G, an apparatus with a digital micro-mirror device and multiple detectors for detecting a feature on an article according to one embodiment is shown. Embodiment 100G is substantially similar to that of 100F. In this embodiment, the digital micro-mirror device 170 may be used to direct and steer different components of the light reflected from the test surface 130 in different directions. For example, the digital micro-mirror device 170 is used to steer light with a first wavelength, e.g., blue light, toward detector 142 while light with a second wavelength, e.g., red light, is steered toward detector 144. It is appreciated that the detectors 142 and 144 may be two different detectors or merely different portions of a single detector.

Figure 1H:
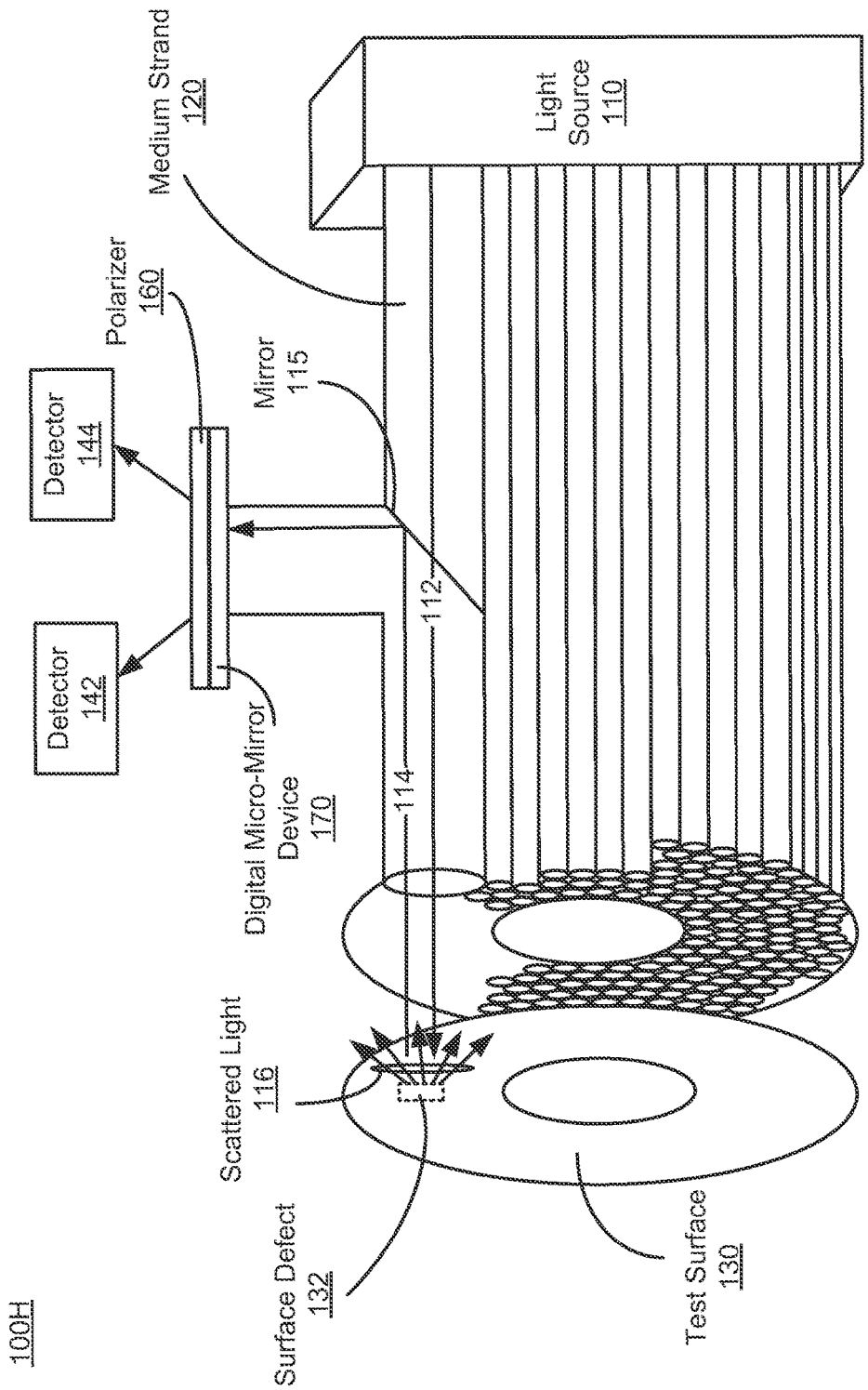
FIG. 1H shows an apparatus with a digital micro-mirror device and a polarizer for detecting a feature on an article according to one embodiment.

Referring now to FIG. 1H, an apparatus with a digital micro-mirror device and a polarizer for detecting a feature on an article according to one embodiment is shown. Embodiment 100H is a combination of embodiments 100G and 100D and operates substantially similar to those embodiments.

Figure 2A:
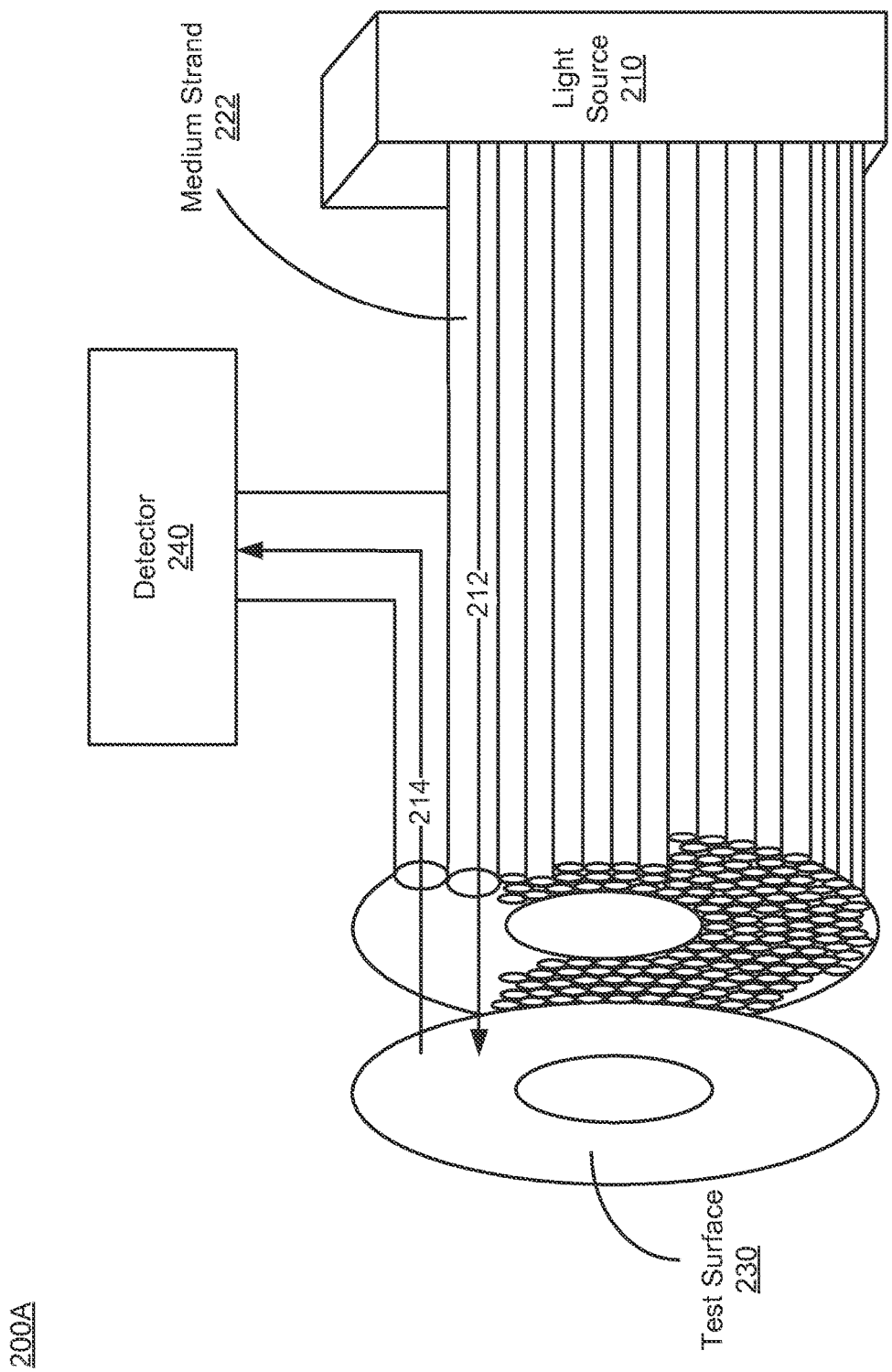
FIGS. 2A and 2B show an apparatus for detecting a feature on a surface of an article according to one embodiment.
Figure 2B:
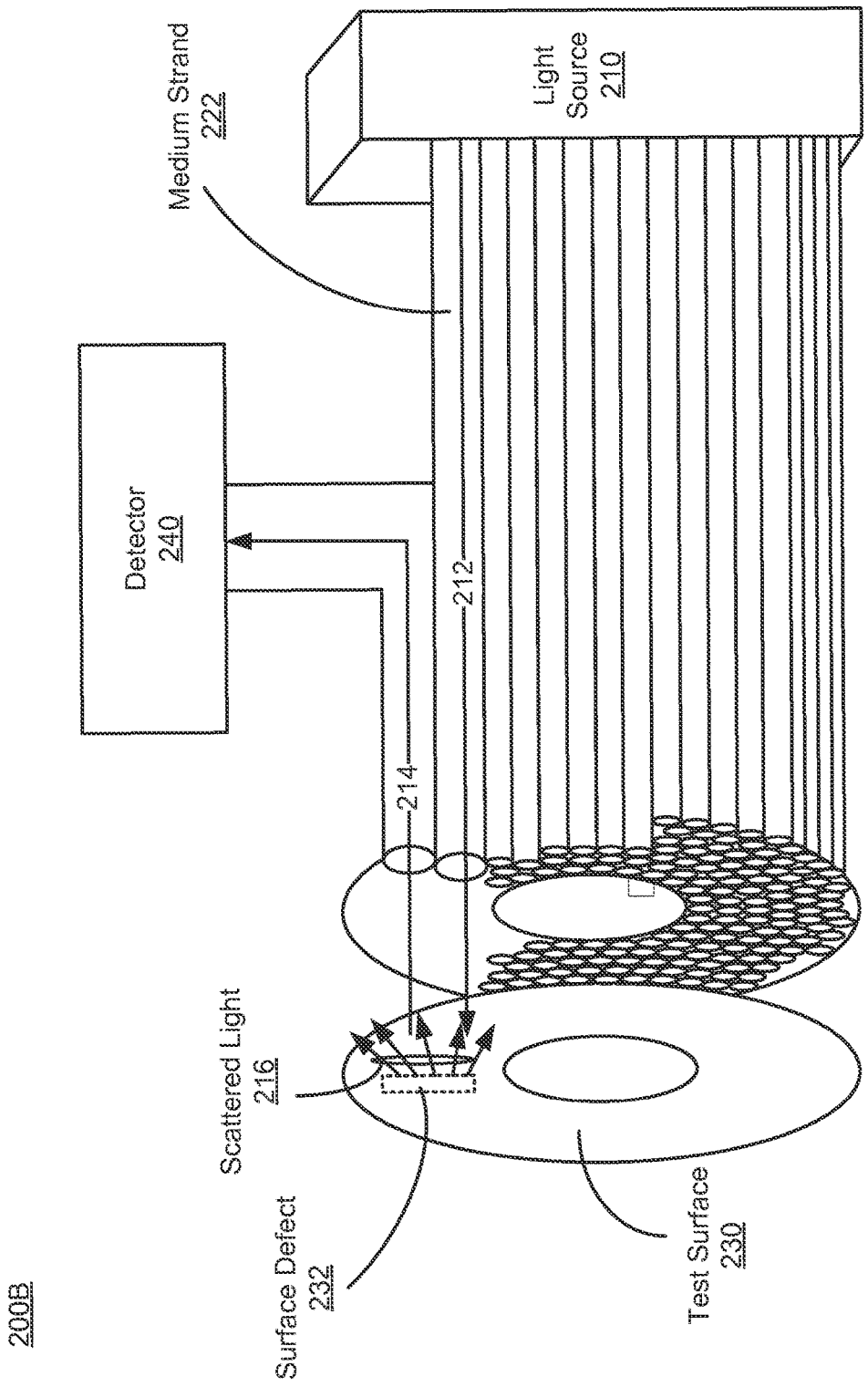

Referring now to FIGS. 2A and 2B, an apparatus for detecting a feature on a surface of an article according to one embodiment is shown. Embodiment 200A operates substantially similar to that of 100A and 100B. As such, like elements are not described any further as they have been described above. However, in this embodiment, the medium strands 222 without mirrors are used. In this embodiment, the incident light 212 is transmitted from the light source 210 to the test surface 230 via one medium strand 222 without a mirror, e.g., half mirror. The light reflected 214 from the test surface 214 is captured and transmitted from the test surface 230 to the detector without using a mirror, e.g., half mirror. Embodiment 200B is similar to embodiment 200A showing a surface defect 232 and scattered light 216 resulting therefrom.

It is appreciated that embodiments 200A and 200B described may similarly include a filter, a polarizer, a digital micro-mirror device, or any combination thereof (not shown) in different positions, e.g., coupled to the detector 240, coupled to the light source 210, etc. It is further appreciated that according to one embodiment, the system may include a combination of a medium strand 222 and a medium strand 120 with a half mirror.

Figure 3B:
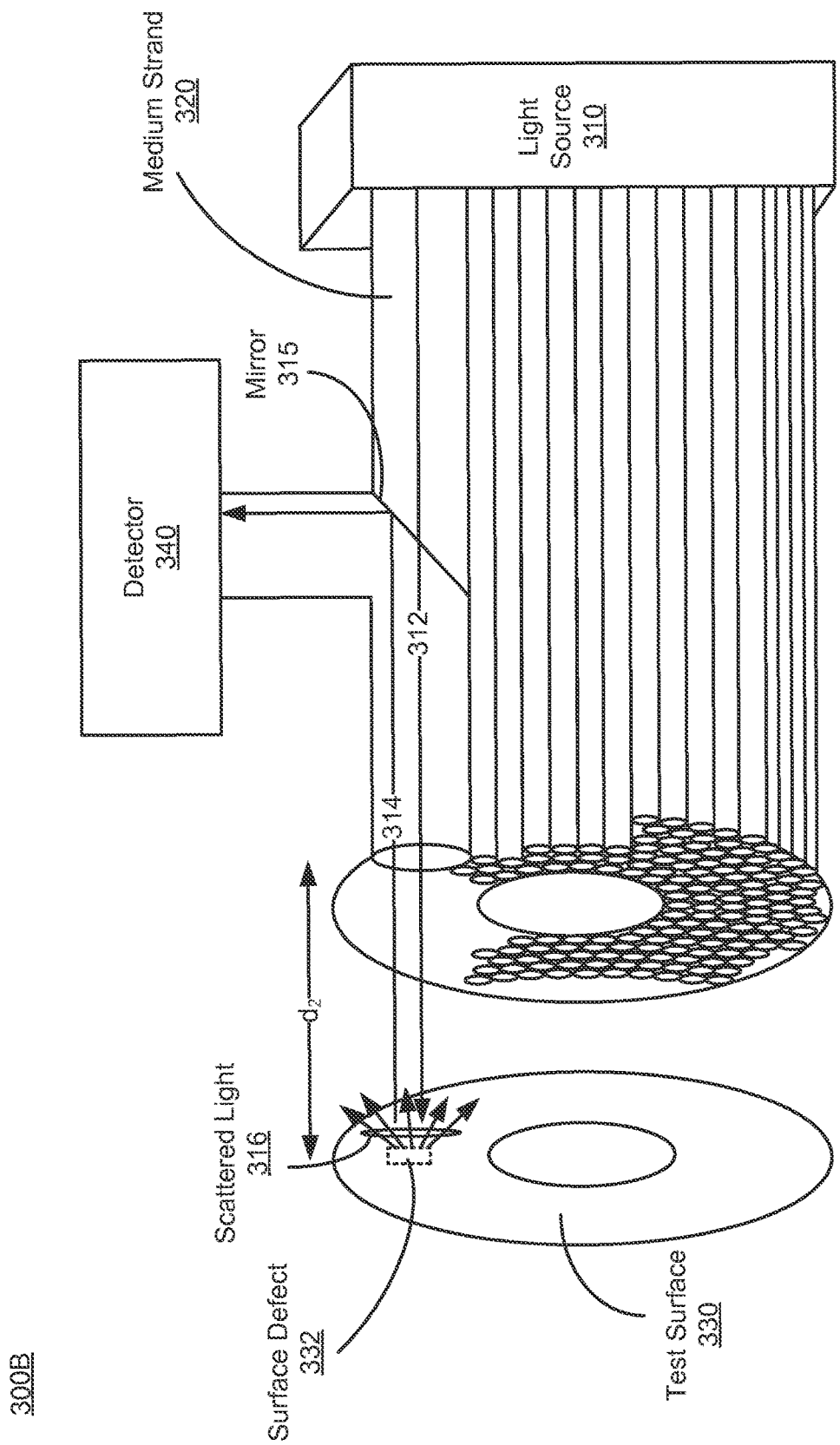

Referring now to FIGS. 3A and 3B, an apparatus for detecting a height associated with a feature on a surface of an article according to one embodiment is shown. Embodiment 300A is similar to that of 100B; however it is appreciated that embodiment 200B may likewise be used for detecting a height associated with a defect of the surface of the article. In this embodiment, the light source 310 is positioned such that the medium strand 320 is positioned at a certain distance, e.g., $d_1$, from the surface of the test surface 330. Incident light 312 is transmitted from the light source 310 to the test surface 330 by passing through the half mirror 315 of the medium strand 320. Light reflected 314 from the test surface 330 may include scattered light 316 that is reflected from the surface of the half mirror 315 toward the detector 340.

In one embodiment, the distance between the medium strand 320 is changed, e.g., $d_2$, from the surface of the test surface 330, as shown in FIG. 3B by repositioning the light source 310. Again, the light source 310 transmits incident light 312 through the half mirror 315 to the test surface 330. The light reflected 314 from the test surface 330 reflects off of the half mirror 315 and is directed to the detector 340. The detector 340 having information from the reflected light at two different distances may determine the height associated with the surface defect 332. The detector 340 may use an interferometer to calculate the height of the surface defect 332. In one embodiment, constructive and destructive interferences may be used resulting from varying the distance between the light source 310 and/or medium strands 320 and the test surface 330 in order to determine the height of the defect.

Figure 3C:
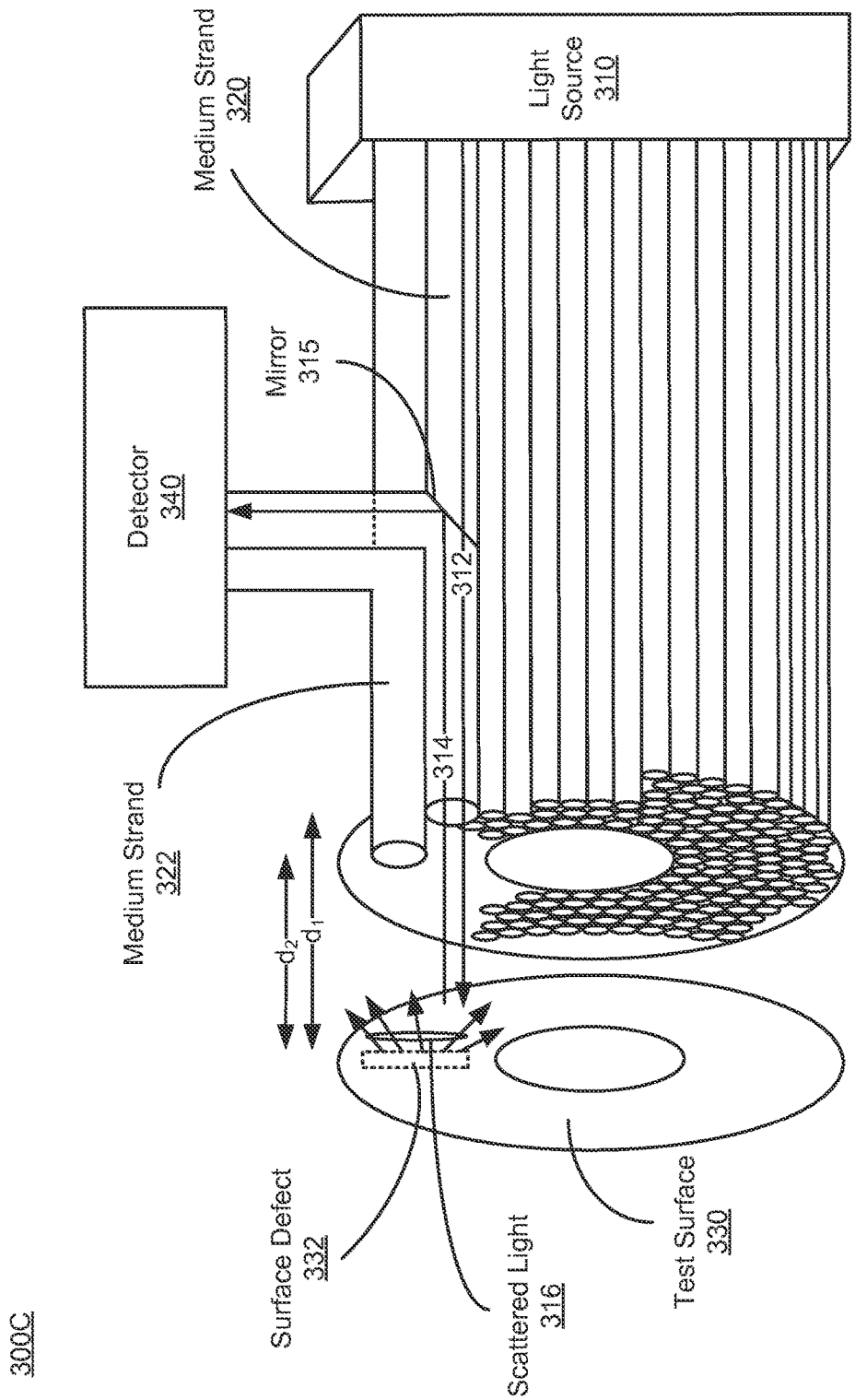
FIG. 3C shows an apparatus for detecting a height associated with a feature on a surface of an article according to another embodiment.

Referring now to FIG. 3C, an apparatus for detecting a height associated with a feature on a surface of an article according to another embodiment is shown. In embodiment 300C, medium strands may have different lengths and are therefore at a different distance from the test surface 330. In this embodiment, medium strand 320 may be at $d_1$ distance from the surface of the test surface 330 while medium strand 322 may be at $d_2$ distance from the surface of the test surface 330. As such, there may be no need to reposition the light source 310 since the medium strands used are in fact at different distances from the test surface 330 and create constructive and destructive interferences to determine the height of the surface defect 332.

Figure 3D:
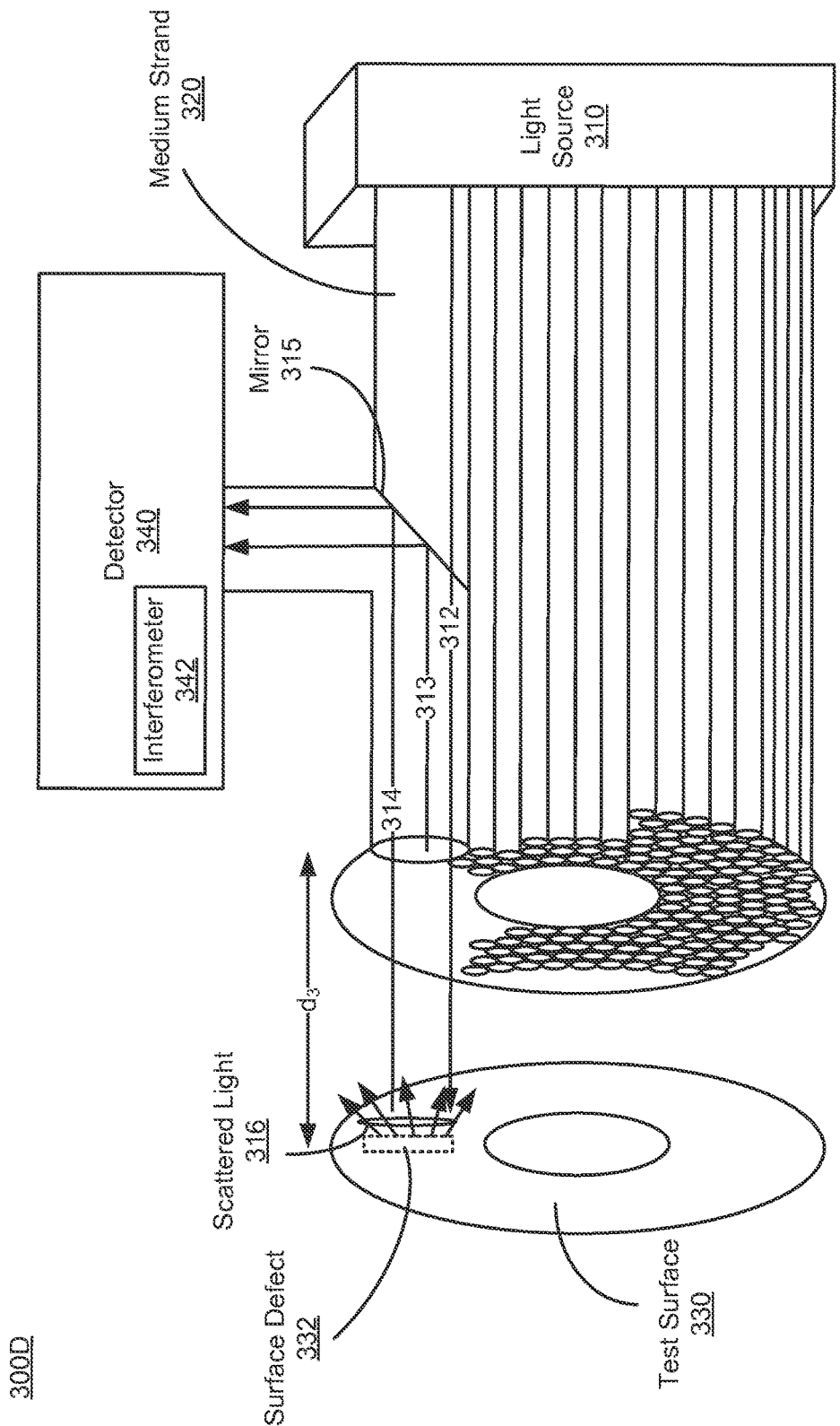
FIG. 3D shows an apparatus for detecting a height associated with a feature on a surface of an article according to yet another embodiment.

Referring now to FIG. 3D an apparatus for detecting a height associated with a feature on a surface of an article according to yet another embodiment is shown. In embodiment 300D, a medium strand 320 is at $d_3$ distance from the surface of the test surface 330. The incident light 312 travels through the mirror 315 and passes from the medium strand environment to the surrounding environment, e.g., air, to get to the test surface 330.

It is appreciated that a small portion of the incident light 312 may be reflected 313 from the interface between the medium strand 312 and the surrounding environment, e.g., air. The light reflected 313 from the interface between the medium strand 320 and the surrounding environment may subsequently be reflected from the mirror 315 and routed to the detector 340. It is appreciated that the light 314 reflecting from the test surface 330 may travel through the surrounding environment and be captured by the medium strand 320. The reflected light 314 may subsequently be reflected from the mirror 315 and routed to the detector 340.

According to one embodiment, the detector 340 may include an interferometer 342. However, it is appreciated that integration of the interferometer 342 with the detector 340 is for illustration purposes only and not intended to limit the scope of the embodiments. The interferometer 342 receives the reflected lights 313 and 314. The two reflected lights 313 and 314 may be amplified in one embodiment. The reflected lights 313 and 314 may form a constructive interference or destructive interference. As such, knowing the distance $d_3$ along with constructive or destructive interference can be used to determine the height associated with the surface defect 332. In one embodiment, the phase shift associated with the reflected lights 313 and 314 along with the knowledge of the distance $d_3$ between the medium strand 320 and the test surface 330 can be used to determine the height associated with the surface defect 332.

According to one embodiment, the apparatus is calibrated prior to determining the height associated with the surface defect 332. For example, the medium strand 320 may be positioned in a control manner at a certain distance away from the test surface 330. Incident light and its reflection may be used at the control distances in order to determine the desired distance, e.g., $d_3$, that the medium strand 320 should be positioned with respect to the test surface 330.

It is appreciated that a filter, a polarizer, a digital micro-mirror device, or any combination thereof may be used in embodiments 300A, 300B, 300C, and 300D based on the application and based on a defect of interest. Furthermore, it is appreciated that the embodiments 300A, 300B, and 300C described above are equally applicable to embodiments where the medium strands do not include a half mirror, as described in embodiments 200A and 200B. It is also appreciated that in some embodiments, a combination of medium strands with half mirror and medium strands without a half mirror may be used to determine the height of the defect.

Accordingly, apparatus and systems described herein for articles such as semiconductor wafers or disks enable a flexible optical design that allows for the simultaneous use of several detectors to cover large areas of the articles under examination to improve the efficiency and resolution; allow vertical integration of various optical components and detectors for an optimized use of a given tool foot-print; utilize a virtually loss- and aberration-free optical path by means of optic fiber arrays; and permit the use of the same optical path for both the incident and reflected light in conjunction with appropriate beam splitters/half mirrors for improved simplicity of the optical design. Such apparatus and systems described herein may be used in-line with a sputtering apparatus for sputtering thin films onto articles, such that articles may be inspected in real time. In an in-line configuration, the second terminus of the optic fiber or a plurality of such optic fibers may be positioned in a sputtering apparatus to examine articles for defects. Such apparatus and systems described herein may be also used at-line with a sputtering apparatus for sputtering thin films onto articles, such that articles may be inspected in real time. In an at-line configuration, the second terminus of the optic fiber or a plurality of such optic fibers may be positioned in a housing proximate to, but outside, a sputtering apparatus to examine articles for defects as they are produced by the sputtering apparatus. Moreover, the apparatus and systems provided herein complement electron and probe microscopy techniques by offering the capability of providing wafer level inspection.

References were made in detail to particular embodiments, examples of which were illustrated in the accompanying drawings. While the embodiments were described in conjunction with the drawings, it is understood that they were not intended to be limiting. The embodiments are intended to cover alternatives, modifications and equivalents. Furthermore, in the detailed description, numerous specific details were set forth in order to provide a thorough understanding. However, it is recognized by one of ordinary skill in the art that the concepts may be practiced without these specific details. In other instances, known methods, procedures, components, and circuits have not been described in detail as to not obscure broader aspects. The foregoing description, for purpose of explanation, has been described with reference to specific embodiments. However, the illustrative discussions above are not intended to be exhaustive or to limit concepts to the precise forms disclosed. Many modifications and variations are possible in view of the above teachings. The implementations described above and other implementations are within the scope of the following claims.

What is claimed is:

1. An apparatus comprising:
a light source configured to shine light onto a surface of an article;
a medium strand configured to contain light and further configured to transmit light, wherein
the medium strand is a fiber optics cable of a plurality of fiber optics cables,
the medium strand comprises a half mirror,
the half mirror is configured to pass light through from the light source to the article, and
the half mirror is configured to reflect light reflected from defects of the article, wherein the light passing through the half mirror is traveling in an opposite direction than the light the half mirror is configured to reflect; and
a detector configured to receive the light reflected from the half mirror, wherein
the detector is further configured to detect defects of the article, and
the medium strand is configured to transmit light from the light source to the article and transmit reflected light from the article to the detector.

2. The apparatus of claim 1 further comprising a filter configured to filter out light of predetermined wavelength.

3. The apparatus of claim 1 further comprising a polarizer configured to pass light of predetermined polarization.

4. The apparatus of claim 1 further comprising a digital micro-mirror device configured to modulate light reflected from the article.

5. The apparatus of claim 1, wherein the medium strand is a 'T' shaped optical fiber having a first terminus, a second terminus, and a third terminus.

6. The apparatus of claim 1, wherein the detector is configured to determine whether the defect is an organic or inorganic defect based on whether the light reflected from the article is elastic or inelastic.

7. The apparatus of claim 1, wherein a distance between the medium strand and the article is varied to determine a height associated with the defect, wherein the determination is made using an interferometer.

8. The apparatus of claim 1, wherein the defect detection is based on light intensity of the light reflected from the half mirror.

* * * * *